United States Patent [19]

Kim et al.

[11] Patent Number: 5,346,696
[45] Date of Patent: Sep. 13, 1994

[54] ASIALOGLYCOPROTEIN - CONJUGATED MEDICINAL AGENT

[75] Inventors: Chung Y. Kim; Hyo S. Lee, both of Seoul, Rep. of Korea

[73] Assignee: Korea Green Cross Corporation, Rep. of Korea

[21] Appl. No.: 983,595
[22] PCT Filed: Jun. 19, 1992
[86] PCT No.: PCT/KR92/00023
 § 371 Date: Feb. 4, 1993
 § 102(e) Date: Feb. 4, 1993
[87] PCT Pub. No.: WO92/22310
 PCT Pub. Date: Dec. 23, 1992

[30] Foreign Application Priority Data

Jun. 19, 1991 [KR] Rep. of Korea .................. 91-10186

[51] Int. Cl.$^5$ ............................................. A61K 37/66
[52] U.S. Cl. ........................... 424/85.4; 424/85.6; 424/85.7; 530/351; 530/395; 435/68.1
[58] Field of Search .................. 424/85.4, 85.6, 85.7; 530/351, 380, 392, 395, 397; 435/68.1

[56] References Cited

U.S. PATENT DOCUMENTS

| | | | |
|---|---|---|---|
| 4,061,538 | 12/1977 | Dorner et al. | 424/85 |
| 4,061,735 | 12/1977 | Funakoshi et al. | 424/177 |
| 4,184,917 | 1/1980 | Dorner et al. | 435/68 |
| 4,217,339 | 8/1980 | Bohn et al. | 424/12 |
| 4,391,746 | 7/1983 | Mitra et al. | 424/101 |
| 4,637,932 | 1/1987 | Pancham | 424/101 |

OTHER PUBLICATIONS

Gustafsson, Marie et al. "Regional Axonal Transport...", Brain Research, 367 (1986) pp. 14–19.
"Methods in Enzymology" Edited by Van Vunakis et al., vol. 70, pp. 159–165 (1980) Academic Press, New York.

*Primary Examiner*—Michael G. Wityshyn
*Assistant Examiner*—C. Sayala
*Attorney, Agent, or Firm*—Lowe, Price, LeBlanc & Becker

[57] ABSTRACT

The present invention relates to a conjugated medicinal agent prepared by combining asialoglycoprotein with a medicine which acts specifically on the liver. The conjugated medicinal agent of the present invention has the following formula (1): P-(S)x-Gal-GA-R, wherein in the P-(S)x-moiety, P is a peptide residue of a human serum glycoprotein and S is a sugar residue of a human serum glycoprotein; Gal is galactose residue; GA is glutaraldehyde residue; x is an integer equal to or greater than 1; and R is a medicinal component selected from the group consisting of interferon, acyclovir sodium, ribavirin, vidarabine, zidovudine, suramin, antisense oligonucleotide, ribozyme, leucovorin calcium, sodium-meglumine diatrizoate, gadolinium-DTPA, glutathione (GSH), prostaglandins, $^{99m}$Tc and $^{131}$I. The present invention also includes a process for preparing the conjugated medicinal agent of formula (I), a pharmaceutical composition containing the conjugated medicine and the use of the conjugated medicine.

19 Claims, 8 Drawing Sheets

ASIALOGLYCOPROTEIN - CONJUGATED MEDICINAL AGENT

TECHNICAL FIELD

The present invention relates to a novel conjugated medicinal agent prepared by combining asialoglycoprotein(ASGP) with a medicinal component which acts specifically on the liver and includes a novel conjugated interferon antiviral agent prepared by combining asialoglycoprotein with recombinant interferon(INF). More specifically, the present invention relates to a novel conjugated interferon which is effective in treating viral hepatitis. The conjugated interferon of the present invention is selectively distributed and absorbed only in the liver, the main site of hepatitis virus replication, and demonstrates potential usefulness as a therapeutic agent for the treatment of B-type and C-type hepatitis. The present invention further relates to a process for preparing the conjugated medicinal agent, a pharmaceutical composition and use thereof.

BACKGROUND ART

Chronic viral hepatitis is a very common disease in the world. It is estimated that approximately 5% of the world population and about 10% of the population in Korea suffer from chronic viral hepatitis. In addition, chronic viral hepatitis arouses medical and social interest since the disease adversely impacts the life, especially the quality and productive aspects of life. Chronic hepatitis generally progresses to liver cirrhosis and possibly primary hepatoma which leads to death. Chronic hepatitis viral infection is the major cause of hepatoma and is considered a highly morbid disease. Therefore, the development of an effective antiviral agent is urgently needed. At present, reliable antiviral therapy for chronic viral hepatitis has yet to be developed. Although some agents have been proven partially effective in the treatment of chronic viral hepatitis, they have many disadvantages, including adverse side effects, which remain to be solved.

As one of the anti-viral agents commonly used in the past adenosine arabinoside monophosphate (Ara-AMP) is a purine-based preparation which exerts strong antiviral activity by inhibiting the activity of DNA polymerase. Early in the 1980's it was reported that Ara-AMP has a therapeutic response of 10 to 17% in the treatment of chronic hepatitis B. However, in 1987 Garcia et al. (Garcia G., Smith C. L., Weissberg J. I., et al.: Adenine arabinoside monophosphate in combination with human leukocyte interferon in the treatment of chronic hepatitis B: A randomized, double-blind, placebo-controlled trial. Ann Intern Med 107:278–285, 1987) reported that the Ara-AMP treatment group did not show any significantly greater effect as compared to the control group. Further, the administration of Ara-AMP sometimes develops very serious adverse effects, such as bone marrow suppression and irreversible neuromuscular pain. Accordingly, Ara-AMP is no longer used in the treatment of chronic viral hepatitis B.

It is generally known that interferon produced by animal cells, i.e. naturally occurring, is effective in the treatment of chronic vital hepatitis B. Natural interferon is a glycoprotein, i.e. a conjugated protein in which the nonprotein group is a carbohydrate of a low molecular weight. It was disclosed as a substance having antiviral activity in 1957. Numerous studies on its action, effect, mechanism of action, method for separation into a purified state, mass production, and the like, have been done in both the industrial and academic fields because of the interest in interferon as an antiviral agent and an anticancer agent. At present, the following kinds of interferon are known:

1) Alpha-interferon, which is induced and produced by vital infection of the leucocytes, has antiviral activity and a natural killer cell-activating effect;
2) Beta-interferon, which is induced and produced by vital infection, especially double-strand RNA virus infection, of the fibroblasts, and has antiviral activity; and
3) Gamma-interferon, which is induced and produced by immunological stimulation of lymphocytes with mitogen or antigen, and has an immunemodulating activity.

Gamma-interferon is reported to have superior anticancer and antiviral activity as compared to the alpha and beta interferons.

Today genetic recombination methods produce recombinant interferon on an industrial scale such that it is widely used for its antiviral and immunomodulator activities.

The therapeutic effect of recombinant interferon for chronic hepatitis B has been reported as 30 to 40% in the West where the prevalence of chronic hepatitis B is relatively low. However, when compared with the spontaneous improvement of 15 to 25% in the untreated group, it is considered that the recombinant interferon is clinically effective in only about 10 to 15% of the chronic hepatitis B patients.

It is estimated that among the world population the hepatitis B surface antigen carrier is approximately 300 million people, of which the Asian population accounts for 80%. When those Asians are treated with recombinant interferon, the remission rate is merely 10 to 15% which is similar to the yearly spontaneous clearance rate of 16 to 17% of hepatitis e antigen. Therefore, a beneficial effect of recombinant interferon may not be recognized in the Asian population, including the Korean population.

It is known that although interferon can remove or reduce the presence of hepatitis B virus(HBV) in serum of the patient with chronic hepatitis B, HBV DNA may remain in the liver cells of some chronic hepatitis patients. Accordingly, a high relapse rate is expected when the treatment with interferon is discontinued.

Meanwhile, it has been reported that although there are minor differences in the dosage and in the treatment period, the use of recombinant interferon shows a therapeutic effect of 28 to 71% for chronic C-type hepatitis when the decrease of serum alanine aminotransferase value, which is obtained from a biochemical liver function test, is used as the criterion for judging the clinical therapeutic effect. However, since approximately half of the patients have a clinical relapse of hepatitis after treatment with recombinant interferon, it is considered that the therapeutic effect of recombinant interferon for C-type hepatitis is only transient. Accordingly, presently commercially available recombinant interferon provides only a transient effect in some B-type and C-type chronic hepatitis patients.

Recombinant interferon, which shows a transient effect in some B and C-type chronic hepatitis patients, unlike natural occurring interferon, is a polypeptide interferon having no sugar groups. Since recombinant interferon is excreted through the kidney into the urine immediately after administration, it has been noted that the uptake rate of recombinant interferon into the liver cells is lower than that of the natural interferon and, therefore, the effect of recombinant interferon is very limited. In practice, it has been determined that the clinical effect of recombinant interferon for B-and C-type chronic hepatitis is only transient in some patients and that both the rate of treatment failure and rate of relapse after cessation of treatment are significantly high. In addition, in order to enhance the therapeutic effect, a large amount of interferon should be administered. However, the use of a large dose is inevitably accompanied by adverse effects such as pyrexia, myalgia, arthralgia and bone marrow suppression. As discussed above, since the prior art recombinant interferon fails to show high efficacy as a therapeutic agent for chronic hepatitis, the development of a novel agent for the treatment of chronic hepatitis with a high therapeutic effect and minimal adverse effects is urgently needed.

The reason why the effect of interferon is transient is that although interferon can reduce virus DNA level in serum, it does not effectively act on viruses present in liver cells. This allows the hepatitis virus to continuously replicate in the liver cells. Therefore, the patients may suffer a recurrence of hepatitis after cessation of treatment with recombinant interferon.

Therefore, the most ideal method of treatment envisioned is drug-target therapy wherein the most effective antiviral agent is introduced directly into the target liver cells.

Methods where the antiviral agent is administered via a receptor specifically present only in the liver cells to inhibit the replication of viruses present in the liver cells have been attempted in the prior art. Fiume et al. (Biochem. Pharm. 35: 967, 1986) has synthesized L-SA-ara-AMP by combining an antiviral agent, 9-$\beta$-D-arabinofuranosyl-adenyl-5'-monophosphate (ara-AMP), with lactosaminated serum albumin (L-SA), which is a novel protein synthesized by conjugation of serum albumin with lactose. It was learned that L-SA-ara-AMP can be specifically absorbed to a high level in the liver cells. However, L-SA-ara-AMP has not had a great effect on the treatment of hepatitis since the method for preparing lactosaminated serum albumin is very complicated and requires the use of albumin which is expensive. In addition, L-SA-ara-AMP is prepared by using a synthetic glycoprotein, which is not naturally present in the human body, and by combining ara-AMP, which is identified as being ineffective for the treatment of chronic hepatitis B.

All plasma proteins, except for albumin, present in blood are a glycoprotein containing a carbohydrate chain which terminates with a sialic acid residue. These plasma proteins are cleared from the circulating bloodstream through a series of processes via cleavage of the sialic acid residues with various enzymes. Neuraminidase exhibits its activity in mammal serum as an enzyme which removes sialic acid residues from glycoprotein (Rosenberg A., Schengrund C. L.:Sialidases. In Rosenberg A., Schengrund C. L.(Eds): Biological roles of sialic acid. New York, Plenum, 1976).

Plasma proteins, which are soluble and which circulate in the blood, lose their solubility and inherent physiological activities after a certain period of time. The mechanism of this action is present in the liver. It is known that the removal of glycoproteins is a function of the liver in view of the fact that when patients are suffering from hepatic cirrhosis or hepatitis and thus have a disorder in the mechanism for removing glycoproteins from the liver cells, the circulating asialoglycoproteins, which are not detected in the normal serum, are present in the serum of these patients. In practice, when desialylated ceruloplasmin is injected into a rabbit, the half life of desialylated ceruloplasmin is 2 minutes which is considerably shorter than 55 hours of the natural ceruloplasmin. This phenomenon is commonly demonstrated in the case of other plasma proteins. Specifically, by removing the sialyl group from the terminal end of the glycoprotein, the galactose group is exposed and recognized by a receptor present in the liver cell membrane resulting in its rapid movement into the liver cell via receptor-mediated endocytosis (RME) and in its disappearance from the circulating bloodstream.

In the 1960's, Morell and Ashwell et al. determined that when a sialyl group of ceruloplasmin is removed by neuraminidase, this plasma protein rapidly disappears from serum. They disclosed that this phenomenon is due to the uptake by the ASGP receptor present in liver cells (J. Biol. Chem., 243:155, 1968). Thereafter, it was reported that the ASGP receptor is present only in liver cells (Adv. Enzymol., 41: 99, 1974). Such specific uptake by liver cells has been identified from the fact that when asialoceruloplasmin or asialoorosomucoid, which is experimentally labelled with tritium, is injected into the living body, the isotope is selectively detected only in liver cells (Scheinberg I. H., Morell A. G., Stockert R. J.: Hepatic removal of circulating proteins. Davidson C. S., ed. Problems in Liver Diseases. pp 279–285, New York, Stratton Company, 1979). In addition, it was also disclosed that this receptor specifically recognizes and absorbs glycoproteins having D-galactose or N-acetylgalactosamin as the terminal sugar group (Ann. Rev. Biochem., 51; 531, 1982). The cell membrane of liver cells comprises a cell structure which combines with asialoglycoprotein terminated with galactose. This cell structure was first named hepato-binding protein (HBP) but is presently called asialoglycoprotein receptor. Further, it has been observed that among various desialylated glycoproteins, the desialylated alpha(1)-acid glycoprotein, asialoorosomucoid, most rapidly disappears from the serum after injection. Therefore, it has been determined that asialo-alpha(1)-acid glycoprotein is both specifically and well taken up by liver cells (FIG. 1) (J. Biol. Chem., 245; 4397, 1970).

Natural interferon which has remarkable antiviral activity is also a glycoprotein containing sialic acid at the terminal end of a carbohydrate chain and it is rapidly cleared from the bloodstream after intravenous injection. Asialo-interferon terminated with galactose, which is prepared by treating naturally occurring interferon with an enzyme to remove the terminal sialyl group, is rapidly cleared from the blood-stream in comparison to naturally occurring interferon, as was also demonstrated in the cases of other glycoproteins including ceruloplasmin.

Figure 2:
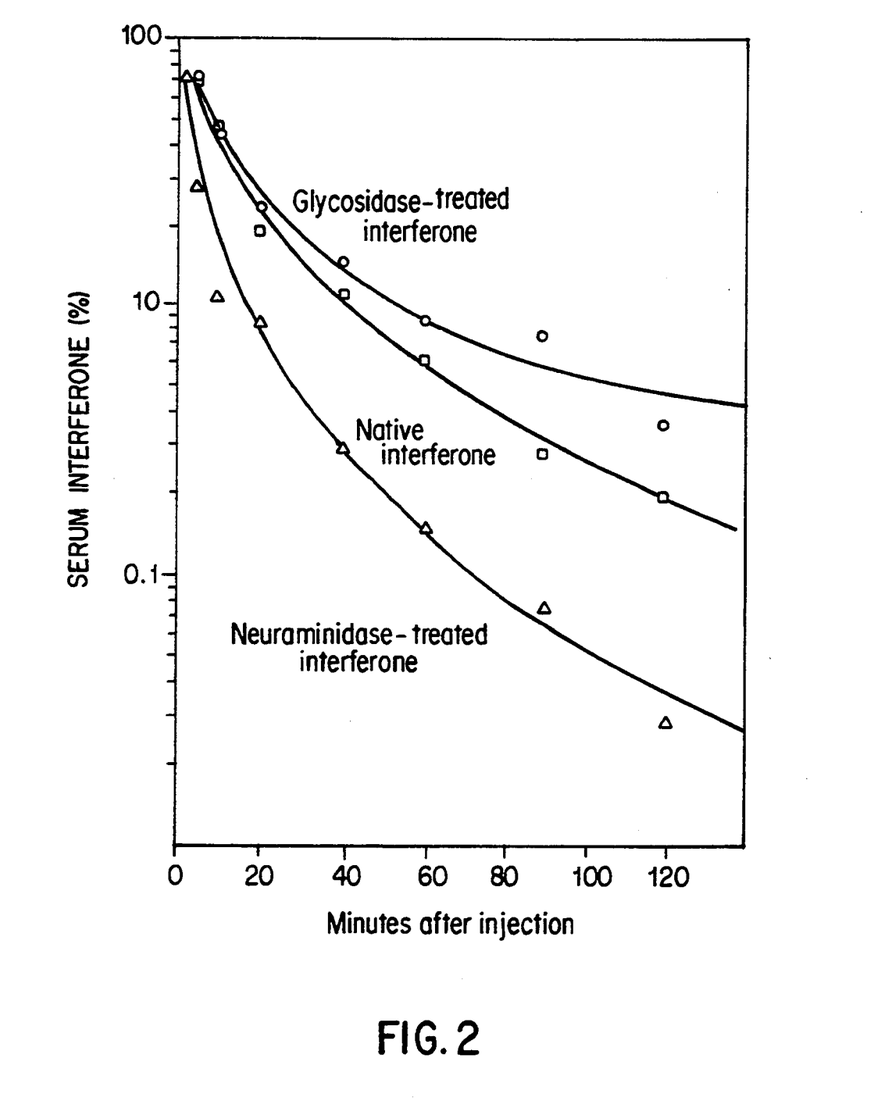
FIG. 2 shows the clearance rates of natural occurring interferon, neuraminidase-treated interferon and glycosidase-treated interferon after intravenous administration.

However, it has been reported that the removal of over 85% of the carbohydrate moiety from the interferon molecule by treatment with glycosidase in order to retain only the polypeptide portion, does not alter the antiviral activity of interferon but reduces the uptake by liver cells which increases the half-life of interferon in the blood (Bose S., Hickman J.: Role of carbohydrate moiety in determining the survival of interferon in the circulation, J. Biol. Chem., 252: 8336, 1977; FIG. 2). Thus, it has been suggested that asialo-interferon, like other asialo-plasma glycoproteins, also passes through a pathway of selective uptake via the asialo-glycoprotein receptor into the liver cells which accounts for its disappearance from the circulating bloodstream.

In 1980, Weissmann et al. prepared a recombinant interferon by manipulation of the INF-$\alpha_{2b}$ gene of the human leukocyte into E. coli. Since recombinant interferon consists only of 165 amino acids and is without carbohydrate chains, the uptake of recombinant interferon into the liver cells is very poor, like the polypeptide interferon formed by treatment of the naturally occurring interferon with glycosidase.

Therefore, it is an object of this invention to target recombinant interferon to the asialoglycoprotein-(ASGP) receptors present specifically in the liver cells to enhance the antiviral activity of the recombinant interferon against the hepatitis viruses which almost exclusively replicate in the liver cells.

It is a further object of this invention to provide an interferon-conjugate which can be administered to mammals, including humans, who show the clinical, serological and molecular biological evidence of hepatitis, to treat hepatitis viral infection, including hepatitis types B, C and D.

It is a further object of this invention to provide a method for treating viral hepatitis by administering to a patient in need, an amount of the conjugated interferon of formula (1), as set forth below, sufficient to inhibit the replication of hepatitis virus present in the liver cells of the patient. It is a further object of this invention to provide a composition for treating viral hepatitis comprising an amount of a conjugated interferon of formula (1), set forth below, effective to inhibit the replication of hepatitis virus present in the liver cells and a pharmaceutically acceptable carrier, adjuvant or excipient therefor.

It is a further object of this invention to provide a method of preparing the novel conjugated antiviral agents by combining asialoglycoprotein(ASGP) with recombinant interferon (INF) resulting in an interferon-conjugate which when parenterally administered to a patient, becomes bound to the ASGP receptor specifically present in the liver cells.

It is an advantage of this invention to provide an interferon-conjugate which reduces the manifestation of adverse reactions relative to the manifestation of adverse reactions of recombinant interferon alone.

The foregoing has outlined some of the more pertinent objects of the present invention. These objects should be construed to be merely illustrative of some of the more pertinent features and applications of the invention. Many other beneficial results can be obtained by applying the disclosed invention in a different manner or modifying the invention within the scope of the disclosure. Accordingly, other objects and a more thorough understanding of the invention may be had by referring to the summary of the invention and the detailed description describing the preferred embodiment in addition to the scope of the invention defined by the claims taken in conjunction with the accompanying drawings.

DISCLOSURE OF INVENTION

In one aspect, the present invention relates to a novel conjugated medicinal agent having the following general formula (I), P-(S)x-Gal-GA-R  (I)

wherein P is a peptide residue of a human serum glycoprotein; S is a sugar residue of a human serum glycoprotein; Gal is a galactose residue; GA is glutaraldehyde residue; x is an integer equal to or greater than 1; and R is a medicinal component as described below.

The medicinal component suitable for preparing the conjugated medicinal agent of the above formula(I) by combining with asialoglycoprotein is substantially all the medicines which act specifically on the liver. Preferably, the medicinal component is: an anti-viral agent for treating B- and C-type chronic viral hepatitis, for example, interferons, acyclovir sodium, ribavirin, vidarabine (adenosine arabinoside), zidovudine (AZT), suramin, antisense oligonucleotide and ribozyme(-catalytic RNAs); a biomodulator for protection from anti-cancer chemotherapy-induced toxicity, for example, leucovorin calcium for methotrexate toxicity; a radiologic contrast for diagnostic liver imaging, for example, sodium meglumine diatrizoate and gadolinium-DTPA; a hepatocyto-protective agent, for example, glutathione(GSH) and prostaglandin; and a radioisotope for liver scanning, for example, $^{99m}$Tc (technetium) and $^{131}$I. More preferably, the medicinal component of the conjugated agent of formula(I) according to the present invention is interferon(INF) which is most effective in the treatment of chronic viral hepatitis. Thus, hereinafter, the present invention will be specifically explained in relation to a conjugated interferon prepared by combining asialoglycoprotein with interferon.

The present invention is directed to certain conjugated-interferons which display an antiviral effect in a human suffering from viral hepatitis and which are targeted to be selectively taken up from the bloodstream flowing through the liver by the liver cells. The conjugated interferons according to the present invention include the conjugated interferons of formula (1), P-(S)x-Gal-GA-INF  (1)

wherein P is a peptide residue of a human serum glycoprotein; S is a sugar residue of a human serum glycoprotein; Gal is a galactose residue; GA is a glutaraldehyde residue; x is an integer equal to or greater than 1; and INF is interferon and preferably INF is recombinant interferon.

The interferon (INF) is alpha-interferon, beta-interferon or gamma-interferon, and is most preferably alpha-interferon.

Alpha(1)-acid glycoprotein (orosomucoid), fetuin, ceruloplasmin, haptoglobin, thyroglobulin, macroglobulin are the preferred human serum glycoproteins.

The P-(S)x-Gal- moiety of formula (1) is preferably a desialylated human serum glycoprotein selected from the group consisting of: asialoorosomucoid, asialofetuin, asialoceruloplasmin, asialohaptoglobin, asialothyroglobulin and asialomacroglobulin.

Another aspect of the present invention is a pharmaceutical composition for treating hepatitis. The composition comprises an amount of a conjugated interferon of formula (1) sufficient to inhibit the replication of hepatitis virus present in the liver cells of a patient affected with viral hepatitis and a pharmaceutically acceptable carrier, adjuvant or excipient therefor. Preferably, the pharmaceutical composition is one suitable for intravenous administration.

Another aspect of the present invention is a method of treating viral hepatitis in a patient suffering from viral hepatitis by administering an amount of a conjugated interferon of formula (1) sufficient to inhibit the replication of hepatitis virus present in the liver cells of a patient affected with viral hepatitis. Preferably, the conjugated interferon is administered by intravenous administration.

Another aspect of the present invention is a process for preparing a conjugated interferon of formula (1)

P-(S)x-Gal-GA-INF  (1)

wherein
P is a peptide residue of a human serum glycoprotein;
S is a sugar residue of a human serum glycoprotein;
Gal is a galactose residue;
GA is a glutaraldehyde residue;
x is an integer equal to or greater than 1; and
INF is interferon and preferably recombinant interferon.

The process comprises the step of providing human blood serum having a glycoprotein of the formula Protein-(Sugar)x-Gal-NANA, characterized in that the second residue from the end of sugar portion is D-galactose (Gal) and the last residue is N-acetyl neuraminic acid (NANA) or (sialic acid). The human blood serum is then treated to separate the Protein-(Sugar)x-Gal-NANA from the human blood serum and recovering the P-(S)x-Ga-NANA. The P-(S)x-Gal-NANA is then treated with neuraminidase to remove NANA and to obtain an asialoglycoprotein (ASGP), P-(S)x-Gal moiety which is a desialylated human serum glycoprotein residue. The asialoglycoprotein, P-(S)x-Gal, is then linked with the interferon by means of a glutaraldehyde (GA) crosslinking method (Reichlin M.: Use of glutaraldehyde as a coupling agent for protein and peptide. Methods Enzymol 70:159–165,1980). The conjugated interferon of formula P-(S)x-Gal-GA-INF (1) is then recovered.

Preferably, the human blood serum is a Cohn fraction V supernatant of human serum and which is treated with DEAE-Sephadex or CM-Cellulose chromatography in a conventionally known manner to separate a Protein-(Sugar)x-Gal-NANA from the Cohn fraction V supernatant.

A more specific process for preparing a conjugated interferon of formula (1)

P-(S)x-Gal-GA-INF  (1)

wherein
P is a peptide residue of a human serum glycoprotein;
S is a sugar residue of a human serum glycoprotein;
Gal is a galactose residue of human serum glycoprotein;
GA is a glutaraldehyde residue;
x is an integer equal to or greater than 1; and
INF is interferon,
comprises providing a Cohn fraction V supernatant of human serum. The Cohn fraction V supernatant of human serum is treated to separate and recover a Protein-(Sugar)x-Gal-NANA glycoprotein therefrom, which is treated with neuraminidase to desialylate the glycoprotein to thereby obtain a glycoprotein residue, asialoglycoprotein (ASGP), having a Protein-(Sugar)x-Gal structure. The asialoglycoprotein is linked with interferon by means of a glutaraldehyde (GA) crosslinking method. The conjugated interferon having Protein-(Sugar)x-Ga-GA-INF structure is then recovered.

Preferably the Cohn fraction V supernatant of human serum is treated with DEAE-Sephadex or CM-Cellulose chromatography in a conventional manner to separate alpha (1)-acid glycoprotein having a Protein-(Sugar)x-Gal-NANA from the Cohn V fraction.

The more pertinent and important features of the present invention have been outlined above in order that the detailed description of the invention which follows will be better understood and that the present contribution to the art can be fully appreciated. Additional features of the invention described hereinafter form the subject of the claims of the invention. Those skilled in the art can appreciate that the conception and the specific embodiment disclosed herein may be readily utilized as a basis for modifying or designing other structures for carrying out the same purposes of the present invention. Further, those skilled in the art can realize that such equivalent constructions do not depart from the spirit and scope of the invention as set forth in the claims.

BRIEF DESCRIPTION OF THE DRAWINGS

For a thorough understanding of the nature and objects of the invention, reference should be had to the following detailed description taken in connection with the accompanying drawings in which.

BEST MODE FOR CARRYING OUT THE INVENTION

In order to reduce the above disadvantages of the prior art recombinant interferon, interferon must enter into the liver cells. Thus, the present invention is able to selectively carry recombinant interferon to liver cells in order that the recombinant interferon is directly available to the liver cells. Thus, plasma glycoproteins are treated with neuraminidase to expose the galactose residue by removing the sialic acid moiety, i.e. form asialoglycoprotein (ASGP). Then the antiviral agent, recombinant interferon, is combined with the exposed galactose residue of glycoprotein (ASGP) such that the combined agent can be bound to the ASGP receptor specifically present in the liver cells. The antiviral agent to be combined includes recombinant alpha-, beta- and gamma-INF, which are known as the most effective agents for treating B- and C-type chronic hepatitis at present.

It is important to note a particular surprising fact in that when alpha, beta or gamma interferon is used alone in the treatment of hepatitis, only alpha interferon is effective. Whereas according to the present invention, when alpha, beta or gamma interferon is combined with asialoglycoprotein(ASGP), each of the interferons, i.e. alpha, beta or gamma interferon, is effective in the treatment of hepatitis.

Furthermore, since the novel conjugated interferon according to the present invention is specifically absorbed only by the liver cells and then retained for a long period in the liver cells, the optimum dosage can be reduced.

Accordingly, adverse effects associated with the administration of frequent doses or large doses of interferon are usually diminished. Although the glycoproteins to be used in preparing the conjugated interferon are not limited to any specific kind, alpha(1)-acid glycoprotein, i.e. orosomucoid, and fetuin, ceruloplasmin, haptoglobin, thyroglobulin and macroglobulin, which are rapidly absorbed into the liver, are preferred as demonstrated at FIG. 1.

The conjugated interferon of the present invention can be prepared by the following method. First, the Cohn fraction V supernatant of human serum is treated with DEAE-Sephadex or CM-Cellulose chromatography in a conventional manner to separate alpha(1)-acid glycoprotein having a Protein-(Sugar)x-Gal-NANA (NANA is N-acetyl neuraminic acid) (Hao Y-L, Wickerhauser M.: A glycoprotein, Biochem. Biophys. Acta 322; 99, 1973), which is then treated with neuraminidase to obtain asialoglycoprotein (ASGP) having a Protein-(Sugar)x-Gal structure with the removal of sialic acid. The asialoglycoprotein is then linked with interferon by means of a glutaraldehyde (GA) crosslinking method to synthesize a conjugate having Protein-(Sugar)x-Gal-GA-INF structure.

The method of the present invention as above is summarized as follows:

TABLE 1

Cohn Fraction V Supernatant of human serum
↓ DEAE-Sephadex or CM-Cellulose Chromatography Alpha (1)-acid glycoprotein
(Protein-(Sugar)x-Gal—NANA)

↓ Treatment with neuraminidase coupled to tresylated support

Asialoglycoprotein
(Protein-(Sugar)x-Gal)

↓ +INF Glutaraldehyde cross-linking method

Asialoglycoprotein-Interferon Conjugate
(Protein-(Sugar)x-Gal—GA—INF)

The glycoprotein used in the above method is a glycoprotein present in human serum. For the purpose of this invention, any glycoprotein, such as alpha(1)-acid glycoprotein (orosomucoid), may be used as long as the second residue from the end of sugar portion of the glycoprotein is D-galactose and the last residue of the glycoprotein is N-acetylneuraminic acid (sialic acid). This also includes such glycoproteins as fetuin, ceruloplasmin, haptoglobin, and the like, which can be used.

Thus, the glycoproteins of orosomucoid, fetuin, ceruloplasmin, haptoglobin, thyroglobulin and macroglobulin, when desialylated are referred to as asialoorosomucoid, asialofetuin, asialoceruloplasmin, asialohaptoglobin, asialothyroglobulin and asialomacroglobulin, respectively, and can be used in the conjugate-interferon of the present invention. These asialoglycoprotein can be prepared by means of the same procedure as the desialylation of alpha(1)-acid glycoprotein, i.e. asialoorosomucoid.

Figure 1:
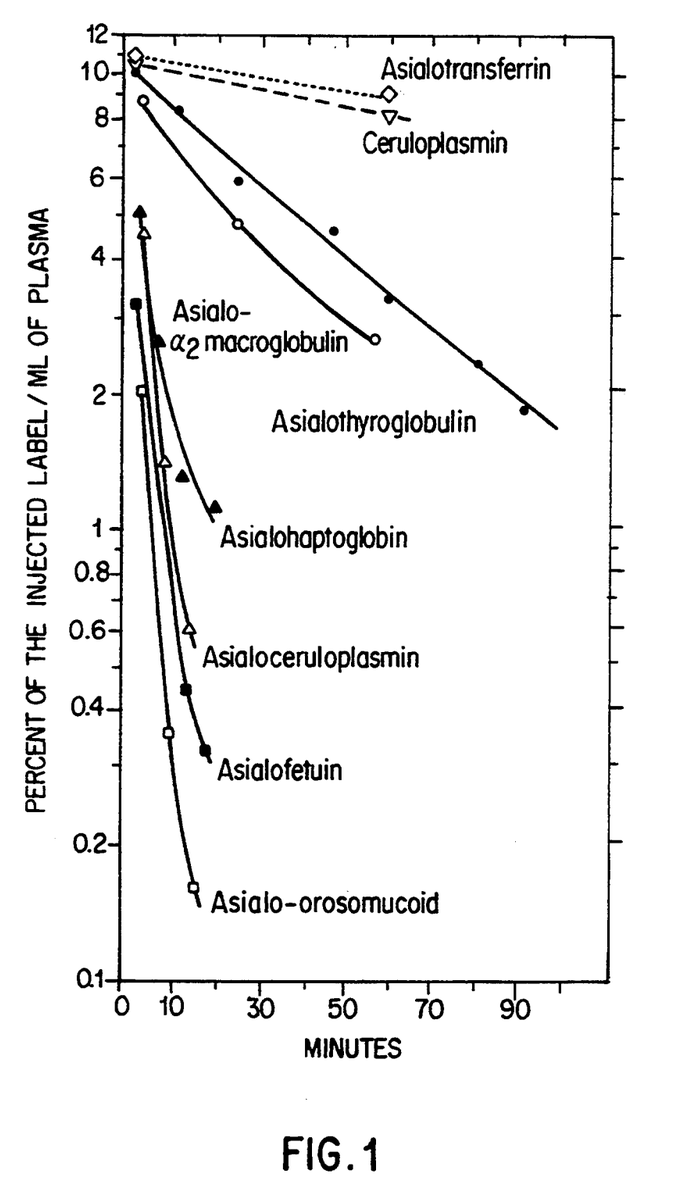
FIG. 1 is a graph which represents the survival of intravenously injected desialylated plasma proteins in plasma.

However, the most preferred one is alpha(1)-acid glycoprotein (asialoorosomucoid) since the percent of asialoorosomucoid remaining in the plasma after injection is about 0.18% per ml of plasma, as see FIG. 1. In order to determine the survival of intravenously injected desialylated plasma proteins, injections (1 ml) were made in the tail vein of male albino rats weighing about 200 g. 1 Ml of each injection corresponds to the following: $^3$H-asialotransferrin, 0.3 mg, $6.6 \times 10^6$ dpm; $^{64}$Cuceruloplasmin, 0.3 mg; $^3$H-asialothyroglobulin, 0.3 mg, $12.6 \times 10^6$ dpm; $^3$H-asialo-$\alpha_2$-macroglobulin, 0.19 mg, $11.2 \times 10^6$ dpm; $^3$H-asialohaptoglobin, 0.12 mg, $9.5 \times 10^6$ dpm; $^3$H-asialoceruloplasmin, 0.3 mg, $6.7 \times 10^6$ dpm; $^3$H-asialofetuin, 0.11 mg, $2 \times 10^6$ dpm; $^3$H-asialoorosomucoid, 0.13 mg, $14.4 \times 10^6$ dpm. Samples of blood were taken at varying time intervals from the tail veins in heparinized tubes and centrifuged, and the plasma radioactivity was determined. Animals were killed, their liver was removed at the times indicated, and aliquots of about 20 mg of wet tissue were used for determination of radioactivity. The result are given in FIG. 1.

FIG. 1 illustrates that the percent remaining of asialo-alpha(1)-acid glycoprotein (asialoorosomucoid), asialofetuin, asialoceruloplasmin and asialohaptoglobin in blood after 12 minutes from being injected intravenously is 0.18, 0.37, 0.6 and 1.2, respectively. Thus, it can be seen that the asialo-alpha(1)-acid glycoprotein, asialoorosomucoid, disappears the fastest from the blood, which indicates that it is absorbed by liver cells at the fastest rate relative to the others.

In the first step for preparing the conjugated interferon of the present invention, Cohn fraction V supernatant can be separated and obtained from human serum according to a conventional method known as the method for the preparation of albumin (Cohn E. J. et al., J. Am. Chem. Soc. 68: 459, 1946). The separation of alpha(1)-acid glycoprotein from Cohn fraction V supernatant and its purification in a large scale are carried out according to a known method (Hao Y-L, Wickerhauser M.; A Simple Method for the Large-Scale Preparation of Alpha(1)-acid glycoprotein, Biochem. Biophys. Acta. 322; 99, 1973) as outlined below.

TABLE 2

```
Cohn Fraction V Supernatant(11 L)
        │ pH 4.7
        │ DEAE-Sephadex(24 g)
        │ 0.025M acetate buffer(2 L)
        │ at −5° C.
   ┌────┴────┐
   ▼         ▼
DEAE cake  Supernatant
   │       Discard
   │ Washed with cold
   │ 0.025M acetate buffer
   ▼
Washed DEAF cake
0.025M acetate
buffer + 1M NaCl        Washings
Stir for 60 min.        Discard
   │
   ▼
DEAE elute(1.2 L)
   │ Ultrafiltration
Concetrate(0.06 L)
   │ Dialyzed against acetate buffer
   │ CM-cellulose chromatography
   ▼
α1-acid glycoprotein(0.82 g)
```

The separated and purified alpha(1)-acid glycoprotein is then subjected to the desialylated reaction according to the following reaction scheme to obtain asialoglycoprotein.

Figure 3:
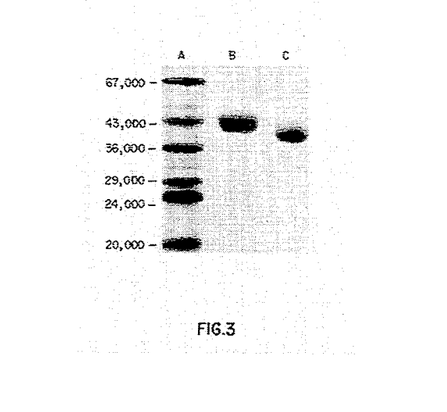
FIG. 3 the electrophoretic diagram of alpha(1)-acid glycoprotein and asialoglycoprotein as separated and purified.

The recovered asialoglycoprotein has the electrophoretic diagram as shown at FIG. 3, column C. FIG. 3, column A illustrates the molecular weight marker of protein, column B shows a single band of 43 kd('kd' means kilodaltons) alpha(1)-acid glycoprotein with the sialic acid residue separated, and column C shows a single band of about 41 kd asialo alpha(1)-acid glycoprotein with the removal of 1.7 kd sialic acid residue.

The final step in preparing the conjugate of asialoglycoprotein with interferon utilizes the glutaraldehyde (GA) cross-linking reaction which is one of the most mild cross-linking reactions. Glutaraldehyde is combined with the exposed amine group in the neutral pH range (6.0–8.0) at 4 to 40 degrees centigrade using a buffer solution with a broad buffer range. This reaction comprises the formation of a Schiff base between the amine group of the protein and the aldehyde group. In this reaction, since glutaraldehyde contains two aldehyde groups, they are combined directly with two amine groups as shown below (Pozmanski M. J. and Juliano R. L.: Biological approaches to the controlled delivery of drugs: a critical review. Pharmacological Reviews 36: 277–336, 1984).

Figure 4:
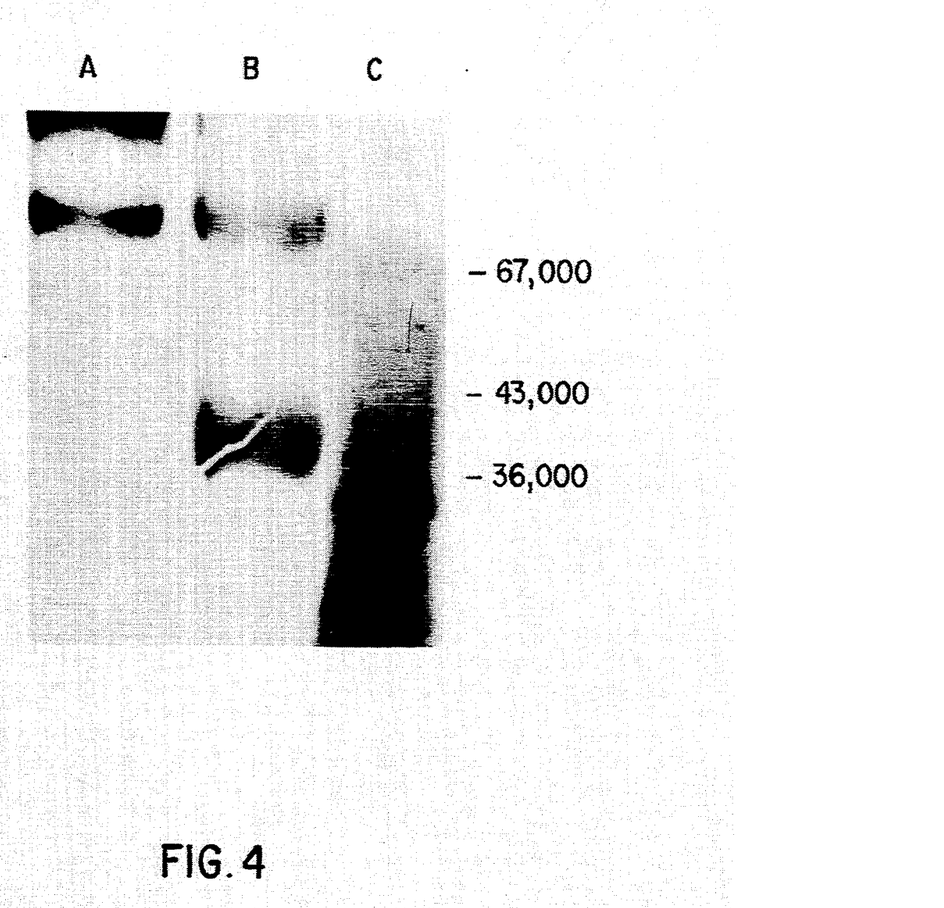
FIG. 4 is the electrophoretic diagram obtained after conjugation of asialoglycoprotein and interferon.
Figure 5A:
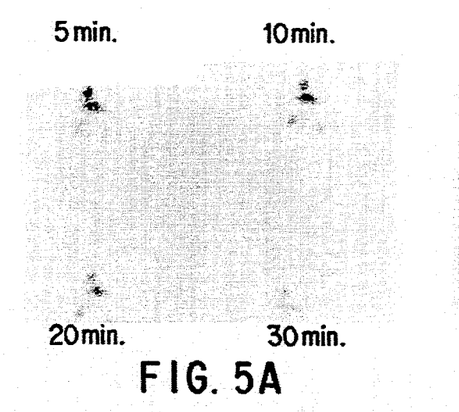
FIGS. 5A–5D show a gamma camera image and the radioactivity graph in which uptakes of bovine serum albumin and asialoglycoprotein in liver are compared.
Figure 5B:
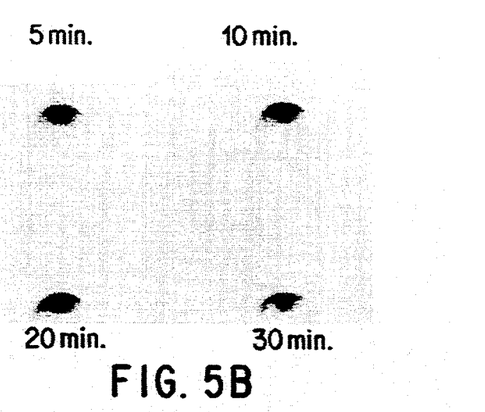
Figure 5C:
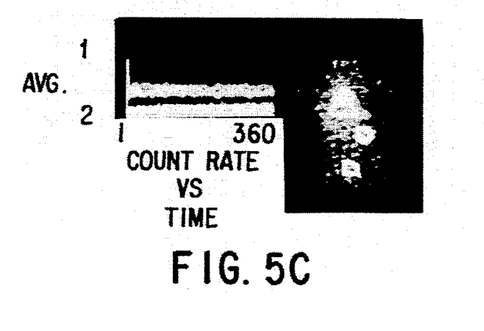
Figure 5D:
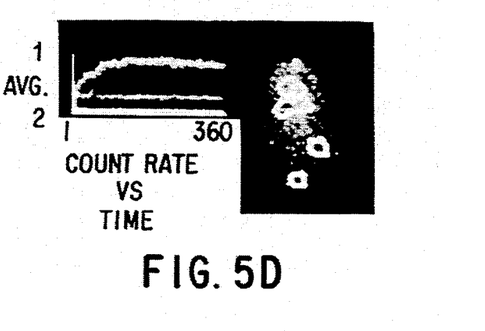
Figure 6A:
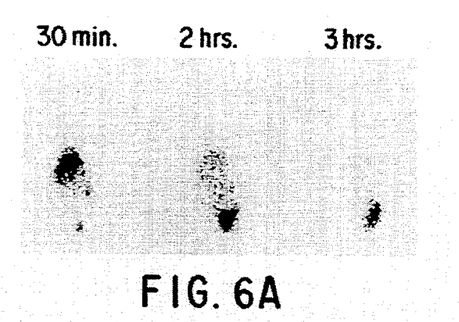
FIGS. 6A–6D show a gamma camera image and a radioactivity graph in which uptakes of interferon and the novel conjugated interferon in the liver are compared.
Figure 6B:
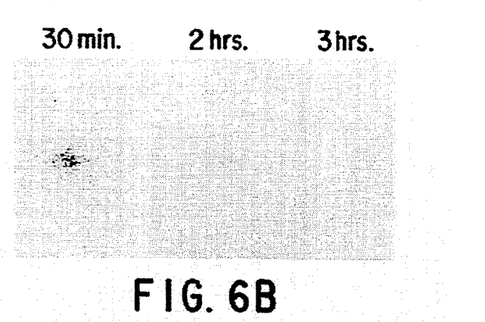
Figure 6C:
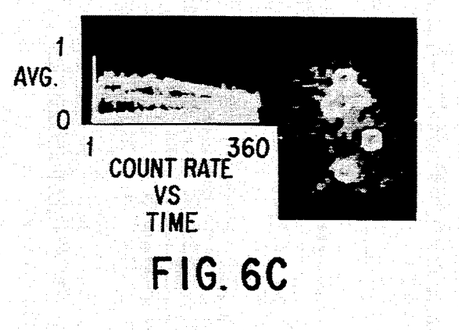
Figure 6D:
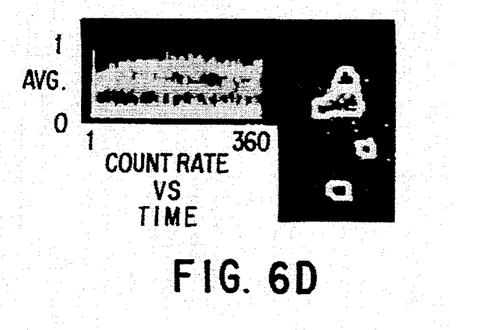

This conjugate can be identified by autoradiation apparatus by first labelling the conjugate with I(131) at the portion of interferon by means of Iodogen method to synthesize I(131)-interferon-asialoglycoprotein conjugate and then subject it to electrophoresis and was stained with Coomassie Blue (FIG. 4; B and C). In FIG. 4, column C represents a marker for the protein molecular weight and column B represents the conjugate as 67kd band and the unreacted asialoglycoprotein after conjugate synthesis as 41 kd band. In addition, column A was obtained from auto-radiography of the electrophoretic gel of column B and shows 67 kd band which corresponds to I(131)-interferon-asialoglycoprotein conjugate.

In order to prove that the asialoglycoprotein used as the carrier for interferon in the present invention is specifically absorbed in the liver, the following animal experiments are conducted. The experiments were divided into two groups according to the purpose as indicated below, and each experiment includes a control group.

Experiment on Tissue Specificity of
Asialo-alpha(1)-acid glycoprotein

Rabbits
↓         ↓
131I—BSA   131I—ASGP
↓
a. Gamma camera image
b. Time course of radioactivity The gamma camera image and the change of radioactivity over time, both of which are obtained from rabbits injected with I(131)-labelled asialoglycoprotein, are compared with those obtained from I(131)-bovine serum albumin (BSA). As a result, it is verified that, as see FIGS. 5A–5D, the purified asialoglycoprotein separated from the human serum is specifically absorbed by the liver. In FIGS. 5A–5D, the upper gamma camera image is a picture of the radioactivity emitted from each organ of the rabbit in a supine position. From this picture, the amounts of asialoglycoprotein present in rabbit organs over time can be comparatively identified. Thus, it can be determined that in comparison with I(131)-bovine serum albumin, I(131)-asialoglycoprotein is more specifically absorbed by the liver and is retained in the liver for a longer period. In the lower graph, the abscissa represents time (X axis), the ordinate (Y axis) represents the radioactivities detected in the liver and the heart, i.e. the bloodstream, respectively. From the image of FIGS. 5A–5D, it can be seen that asialoglycoprotein is more markedly and specifically absorbed in the liver relative to albumin.

Experiment on Liver Selectivity
of conjugated interferon

Rabbits
↓         ↓
131I—INF   131I—INF—ASGP Conjugate
↓
a. Gamma camera image
b. Time course of radioactivity
c. Biodistribution The gamma camera image and the radioactivity in the liver, heart and bladder over time, both of which were obtained from a rabbit injected with I(131)-labelled interferon, are compared with those obtained from the I(131)-labelled conjugate interferon of the present invention. The result thereof is shown in FIGS. 6A–6D.

From the gamma camera images of FIGS. 6A–6D, it can be seen that interferon was retained mainly in the liver for up to 30 minutes after the injection but its excretion into the bladder had already started. After 3 hours, interferon is substantially not present in the liver but is present mainly in the bladder. Meanwhile, the asialoglycoprotein-interferon conjugate of the present invention was continuously retained mainly in the liver for 30 minutes, 2 hours and 3 hours after the injection, and excretion into the bladder was not observed. This also complies with the change in radioactivities over time as represented in the lower graph. Thus, in the case of interferon, both the liver radioactivity in the top line and the blood radioactivity in the middle line gradually decreased within 30 minutes and then the bladder radioactivity in the low line increased. In contrast, in the asialoglycoprotein-interferon-injected group the liver radioactivity was continuously maintained and no increase in the bladder radioactivity was observed.

Figure 7:
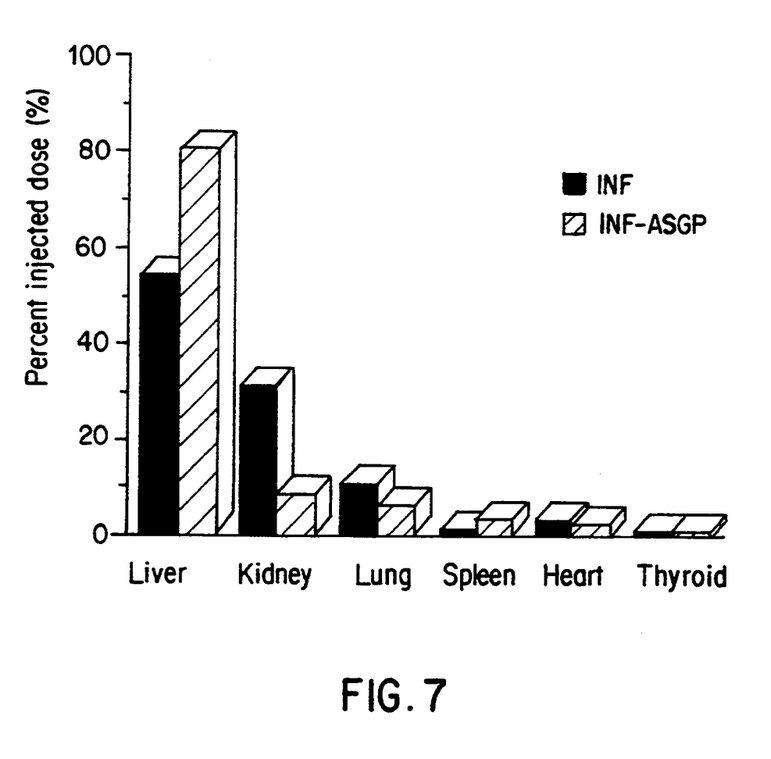
FIG. 7 is a graph which represents the biodistribution of interferon and the novel conjugated interferon in the living body 3 hours after administration.

In order to compare the tissue specificity of the novel conjugated interferon with that of interferon, interferon and asialoglycoprotein-interferon conjugate are each injected into a rabbit and, after 3 hours, the rabbit is sacrificed. The radioactivity in each organ is determined and the distribution in rabbit tissues was compared, as see FIG. 7.

As a result, upon reviewing the relative survival rate in each organ on condition that all radioactivities retained in six organs, i.e. liver, kidney, lung, spleen, heart and thyroid totaled 100, in the case of asialoglycoprotein-interferon conjugate the liver survival amount is about 85% of the total survival amount in all organs and the survival rates in the kidney, lung and heart are only a mere 7%, 5% and 1%, respectively. In contrast, in the case of interferon the survival rate in the liver is only 53% and the survival rates in the kidney, lung and heart are relatively high, i.e. 32%, 11% and 2%, respectively.

Figure 8:
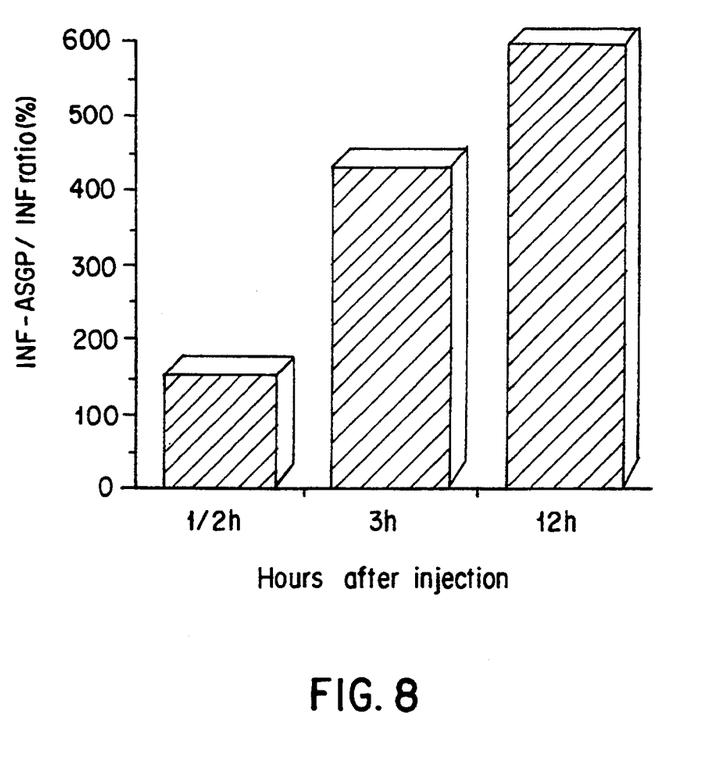
FIG. 8 is a graph which represents the relative biodistribution of interferon and the novel conjugated interferon in the liver over a period of time.

FIG. 8 is a graph showing the relative survival rates of interferon and the novel conjugated interferon in the liver overtime. From this figure, it can be seen that the survival of asialoglycoprotein-interferon conjugate in the liver is significantly higher and longer than that of interferon. That is, the survival of the asialoglycoprotein-interferon conjugates is 1.5, 4.3 and 6 times higher than interferon at 30 minutes, 3 hours and 12 hours, after injection, respectively.

The interferon conjugate of the present invention can be formulated into an injectable composition for the treatment of hepatitis in combination with pharmaceutically acceptable carriers conventionally used for interferon preparations, such as adjuvants, stabilizers, buffering agents and the like. The buffering agent suitable for this purpose is preferably sodium phosphate, potassium phosphate, etc. The composition of the present invention may further include a preservative such as phenol, a stabilizer such as albumin, L-cystein hydrochloride, maltose, sodium chloride or potassium chloride, and the like.

Although the dosage may be varied depending on the age and body weight of the patient, the condition of disease, and the like, in general the conjugate interferon of the present invention is intravenously injected in an amount of 0.2 to 2 million international units on the basis of interferon per square meter of body surface, one time for one or two days. However, the administration period and amount may be adjusted in accordance with the administration method of other conventional interferon preparations as appreciated by those skilled in the art.

The conjugated interferon of the present invention is specifically absorbed by the liver cells and is retained for a long time in the liver. Accordingly, the dosage of the conjugated interferon can be significantly reduced in comparison with the conventional interferon formulations. Such reduced dosage will make the subject patient free from the adverse effects due to interferon itself, such as fever, myalgia, bone marrow suppression, and the like. Therefore, the human tolerance of the conjugated interferon according to the present invention is significantly better than that of conventional interferons.

Subjects showing clinical, serological and molecular biological signs of viral hepatitis are given the drug. Positive reactions for HBsAg and anti-HCV are the hallmark of the chronic hepatitis, B and C, respectively. The composition of the drug is set forth above and the results of intravenous administration are presented at FIGS. 7 and 8.

The following examples are given with the intention of more specifically explaining the present invention but do not limit the scope of the present invention in any way. In the examples, unless otherwise specified, the interferon is recombinant alpha-interferon.

PREPARATION OF ASIALOGLYCOPROTEIN (PROTEIN-(SUGAR)X-GALACTOSE)

EXAMPLE 1

Preparation of asialoglycoprotein from alpha(1)-acid glycoprotein

1. Preparation of tresylated support

10 G of wet Sepharose 4B (Pharmacia) is transferred into a glass filter and then successively washed with 100 ml of 30%, 60%, 80% (v/v) aqueous acetone solution and 100% absolute acetone. Washed Sepharose 4B gel is introduced in a dry beaker containing 30 ml of absolute acetone and 150 ul (u=micro) of tresyl chloride (Fluka A. G., Buchs, Switzerland) while stirring with a magnetic bar. After the beaker is allowed to stand at room temperature for 10 minutes, the whole mixture is transferred again into the glass filter and then washed with 70%, 50% and 30% (v/v) solution of acetone dissolved in 50 mM HCl and finally with 1 mM HCl. The resulting product is stored at 4 degrees centigrade or otherwise treated with acetone, dried and then stored at room temperature. The support thus obtained can support about 450 umol of enzyme per 1 g of the dry gel.

2. Binding the neuraminidase to the tresylated support

1 Ml (0.4mg/ml) of neuraminidase (Sigma Chem.) is passed through a NAP TM -10 Column (Pharmacia) and then is dissolved in 1.5ml of 0.2 M sodium phosphate —0.5M NaCl buffer (pH 7.0) (A$_{280}$=0.534) and 1.0 g of activated tresyl-Sepharose 4B is added thereto. The mixture is shaken slowly for 16 hours at 4 degrees centigrade and 1.5 ml of 0.5 M tris buffer (pH 7.5) is added thereto. The whole mixture is placed at 4 degrees centigrade for 5 hours to complete the reaction. The obtained gel is washed with 0.1 M sodium phosphate-0.15M NaCl (pH 5.5) to obtain neuraminidase-Sepharose 4B which is then stored at 4 degrees centigrade (A$_{280}$=0.45) (yield of neuraminidase in the buffer: OD 0.084/OD0.534=0.064 mg/0.4 mg=16%).

3. Preparation of asialo alpha(1)-acid glycoprotein

250 Mg of alpha(1)-acid glycoprotein is dissolved in 25 ml of 0.15 M NaCl-0.1 M sodium acetate buffer (pH 5.5) and then the obtained solution is mixed with a solution of 200 mg of neuraminidase-Sepharose 4B dissolved in 2 ml of the same buffer. The mixture is allowed to react overnight at 37 degrees centigrade. The elute is obtained and then the efficiency of desialylation is determined according to a thiobarbituric acid analysis (Warren L: The thiobarbituric acid assay of sialic acids. J Biol Chem 234: 1971-1975, 1959). Thus 1.0 ml of alpha(1)-acid glycoprotein solution (10 mg/ml) treated with neuraminidase-Sepharose B is treated with a NAP TM -10 Column to remove the salt. Then, 50 ul of 1N H$_2$SO$_4$ is added to 1 ml of the elute and the mixture is shaken, incubated for 1 hour at 80 degrees centigrade and then cooled down to remove a sialic acid group from the alpha(1)-acid glycoprotein, which still contains sialic acid group after neuraminidase treatment. 0.2 Ml of the sample is thoroughly mixed with 0.1 ml of periodate and the mixture is allowed to stand for 20 minutes, and after the addition of 1.0 ml of arsenite, is shaken until the yellowish-brown color disappears. To the resulting solution is added 3 ml of thiobarbituric acid, and the whole mixture is boiled for 15 minutes and then cooled down in ice-water for 5 minutes. A 2.0 ml aliquot of the mixture is mixed with 2 ml of cyclohexanone. After centrifugation of the mixture for 3 minutes, the absorbance of red supernatant is measured at 549 nm wavelength. The absorbance of the control alpha(1)-acid glycoprotein is 0.008 and the absorbance of the sample asialo-alpha(1)-acid glycoprotein is 0.118.

Therefore, the absorbance of pure sialic acid is 0.110 (0.118-0.008)O.D. The molecular absorbance index of sialic acid is 57,000 and the released amount(umol) of sialic acid can be calculated using the following equation:

$$\frac{V \times O.D._{549}}{57,000} \times 1000 = \frac{V \times O.D._{549}}{57} =$$

$$\frac{4.3 \times O.D._{549}}{57} = 0.075 \times O.D._{549}$$

V is the amount of thiobarbituric acid,
1000 convert ml to liter amounts and
O.D. means optical density.

The amount of sialic acid released from asialoglycoprotein with sulfuric acid is 0.00825 umol (=0.075×0.110). One (1) ml of alpha (1)-acid glycoprotein (1 mg/ml) contains 0.369 umol of sialic acid. Then, since the amount of alpha(1)-acid glycoprotein used in the experiment is 2 mg, the total amount of sialic acid is 0.738 umol (=0.369 umol×2) and the amount of sialic acid released with neuraminidase is 0.7298 umol (=0.738−0.0082). Therefore, the efficiency is calculated as 0.7298/0.738×100=99%.

EXAMPLE 2

According to the procedure as set forth at Example 1, fetuin, ceruloplasmin, haptoglobin and thyroglobulin are used in place of alpha(1)-acid glycoprotein to prepare asialofetuin, asialoceruloplasmin, asialohaptoglobin and asialothyroglobulin, respectively.

EXAMPLE 3

Preparation of the conjugate of asialo alpha(1)-acid glycoprotein and recombinant interferon (Protein-(Sugar)x-Galactose-Glutaraldehyde-Interferon)

The synthesis of the conjugate is carried out in the following manner by means of the one-step method of Harlow and Lane (1988). 1.0 Ml of I(131)-labelled interferon (150 ug/ml) is treated with a NAP ™-10 Column to change the buffer solution 0.5 M sodium phosphate, pH7.5 into 0.1 M sodium phosphate, pH 6.8. The obtained solution is transferred into a tube containing a small magnetic stirring bar into which 100 ul (0.6 mg) of asialo alpha(1)-acid glycoprotein is introduced. In a hood, 100 ul of 1% glutaraldehyde is added dropwise over one minute to the mixed solution in the tube while stirring. The whole mixture is incubated for 3 hours at room temperature and 100 ul of 1M ethanolamine (pH 7.2) is then added. Then, the mixture is incubated again for one hour at room temperature and separated by a liquid chromatography (FPLC) using Sepharose 12 Column to obtain two fractions at 214nm. The isotope level of the first I(131)-labelled interferon is 86.1 uCi, and the isotope levels in the first and second fractions are 6 uCi and 6 uCi, respectively. Electrophoresis provides three bands; the light and wide band larger than 70 kd which represents polymerized conjugates, the 67 kd conjugate band and the 41 kd band of asialoglycoprotein remaining after the reaction can be identified. The gel after electrophoresis is subjected to autoradiography to identify two bands, i.e. the dense and wide band of the polymerized conjugate over 70 kd and the 67 kd conjugate band. The conjugate of asialoglycoprotein and I(131)-labelled interferon used in the experiment using a rabbit corresponds to the first 67 kd fraction separated with FPLC.

EXAMPLE 4

According to the procedure as set forth at Example 3, asialofetuin, asialoceruloplasmin, asialohaptoglobin and asialothyroglobulin are used in place of asialo alpha(1)-acid glycoprotein to prepare the conjugates of the above asialo plasma proteins and interferon.

TEST EXAMPLES

The following animal tests intend to identify the tissue specificity of asialo alpha(1)-acid glycoprotein and to compare the liver cell specificity of the conjugate interferon of the present invention.

A. Preparation of the sample for comparative testing

According to the method of Franker and Speck (Biochem. Biophys. Res. Commun. 80:849-857), interferon, bovine serum albumin and asialo alpha(1)-acid glycoprotein are iodized to prepare the radioactive iodized, ($^{131}$I) natural interferon, bovine serum albumin and asialo alpha(1)-acid glycoprotein having the following specific activities, which are used as samples in the animal test.

Specific activity of iodized interferon:

359 uCi/15 ug = 23.9 uCi/ug

Specific activity of iodized bovine serum albumin:

400 uCi/30 ug = 13.3 uCi/ug

Specific activity of iodized asialo alpha(1)-acid glycoprotein:

1607 uCi/60 ug = 26.8 uCi/ug

B. Test Method and Results

TEST 1

Test for the tissue specificity of asialo alpha(1)-acid glycoprotein

Rabbits weighing 1.5 to 2.0 kg were subjected to general anesthesia and I(131)-labelled iodized bovine serum albumin or iodized alpha(1)-acid glycoprotein was injected into the ear veins. Thereafter, the image of the interested section established by an image computer is taken by a gamma-camera in one point every five seconds, so that the radioactivity in each organ was measured. The camera used is an Ohio Nuclear ™ 410 gamma camera equipped with a collimator having a high resolving power. The photographs were taken every 5 minutes and therefore six photographs were obtained during 30 minutes. The image photographs thus obtained correspond to FIG. 5A-5D. The image photographs of FIG. 5A-5D in the upper panel show that I(131)-asialo alpha(1)-acid glycoprotein is more specifically absorbed by the liver in comparison to I(131)-bovine serum albumin. In the lower panel of FIGS. 5A-5D, the abscissa represents time, the upper line represents the radioactivity detected in the liver and the lower line represents the radioactivity in the heart, i.e., the bloodstream. From these graphs, it can be seen that asialo alpha(1)-acid glycoprotein is specifically taken up in the liver.

TEST 2

Comparative test for liver specificities of interferon and the conjugated interferon of the present invention According to the same manner as described in TEST 1, above, I(131)-interferon and I(131)-asialo alpha(1)-acid glycoprotein conjugate were injected into the ear veins of rabbits. In order to comparatively measure the radioactivity in the liver, the photograph for 300,000 counts was taken every 30 minutes to obtain six photographs during 3 hours. The image photographs are presented at FIGS. 6A-6D. From the gamma camera images at FIGS. 6A-6D, it can be seen that interferon is retained mainly in the liver up to 30 minutes after being injected. Thereafter, it is excreted into the bladder via the kidney. In addition, 3 hours after the injection, interferon is substantially not present in the liver but is mainly present in the bladder. However, in the case of asialo alpha(1)-acid glycoprotein-interferon conjugate, it is retained in the liver after 30 minutes, after 2 hours and even after 3 hours and its presence in the bladder is not observed.

Upon comparing the lower panels of FIGS. 6A-6D, in the case of interferon, the liver radioactivity shown in the top line and the blood radioactivity shown in the middle line gradually decreased creased within 30 minutes and then the bladder radioactivity shown in the low line is increased. Whereas, in the case of asialo alpha(1)-acid glycoprotein conjugate the liver radioactivity is continuously maintained and no increase in the bladder radioactivity is observed. The above test establishes that the survival time of the interferon conjugate of the present invention in the liver is remarkably longer than that of natural interferon.

TEST 3

Comparison of biodistribution of interferon and the conjugated interferon of the present invention in tissues After the above TEST 2 is completed, the rabbits were sacrificed and the liver, kidney, lung, spleen, heart and thyroid were removed from the rabbits. The radioactivity distributed in each organ was measured to calculate the amount of interferon distributed therein. The result thereof is presented in FIG. 7.

From the above tests, it can be seen that the penetration of the interferon conjugate of the present invention into the liver is stronger than that of conventional interferons and the conjugate is retained in the liver for a significantly longer period and therefore its pharmacological effect can last for a significantly longer period.

Composition Examples

FORMULATION EXAMPLE 1

| | |
|---|---|
| Asialoorosomucoid-alpha-interferon conjugate | 500,000 I.U.* |
| Sodium Chloride | 8.0 mg |
| Dibasic sodium phosphate | 1.74 mg |
| Monobasic potassium phosphate | 0.2 mg |
| Potassium Chloride | 0.2 mg |
| Phenol | 3.3 mg |
| Albumin (human) | 1.0 mg |

The above components are dissolved in sterile distilled water for injection sufficient for forming a solution and the resulting solution is placed in a sterile vial (1 ml) and stored at 2 to 10 degrees centigrade.

*International Units of interferon activity.

FORMULATION EXAMPLES 2-4

In place of asialoorosomucoid-alpha-interferon conjugate used in the Formulation Example 1, asialofetuin-interferon conjugate 500,000 I.U., asialoceruloplasmin-interferon conjugate 600,000 I.U. or asialohaptoglobin-interferon conjugate 1,000,000 I.U. is mixed with the same preservative, buffering agent and stabilizing agent as those of Formulation Example 1. The mixture solubilized with sterile distilled water for injection and the solution is placed into a sterile 1 ml vial for injection and stored as described above in Formulation Example 1.

FORMULATION EXAMPLE 5

Asialoorosomucoid-beta-interferon conjugate . . . 1,000,000 I.U.

| | |
|---|---|
| Sodium Chloride | 9.0 mg |
| Albumin (human) | 5.0 mg |
| Phenol | 3.0 mg |

The above components are dissolved in sterile distilled water for injection sufficient to form a solution and the resulting solution is placed in a sterile vial (1 ml) and stored at 2 to 10 degrees centigrade.

FORMULATION EXAMPLE 6

Asialoorosomucoid-gamma-interferon conjugate 500,000 I.U. is substituted for the asialoorosomucoid-beta-interferon conjugate of Formulation Example 5 and is mixed with the same adjuvants and the solution is placed in a sterile vial (1 ml) for injection.

The formulations prepared by above formulation examples are suitable for intravenous injection.

The present disclosure includes that contained in the appended claims as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

What is claimed is:

1. The asialoglycoprotein-conjugated medicinal agent having the following formula (1), P-(S)x-Gal-GA-INF    (1)

wherein

P is a peptide residue of a human serum glycoprotein;
S is a sugar residue of a human serum glycoprotein
Gal is a galactose residue;
GA is a glutaraldehyde residue;
x is equal to or greater than 1; and
INF is interferon.

2. The conjugated medicinal agent of claim 1, wherein INF is alpha interferon.

3. The conjugated medicinal agent of claim 1, wherein INF is beta interferon.

4. The conjugated medicinal agent of claim 1, wherein INF is gamma interferon.

5. The conjugated medicinal agent of claim 1, wherein said P-(S)x-Gal- is a desialylated human serum glycoprotein residue in which P is a protein residue of a human serum glycoprotein, S is a sugar residue of a human serum glycoprotein and Gal is a D-galactose residue.

6. The conjugated medicinal agent of claim 5, wherein said desialylated human serum glycoprotein is selected from the group consisting of asialoorosomucoid, asialofetuin, asialoceruloplasmin, asialohaptoglobin, asialothyroglobulin and asialomacroglobulin.

7. The conjugated interferon of claim 1, wherein INF is recombinant interferon.

8. A pharmaceutical composition for treating hepatitis comprising an amount of a conjugated recombinant interferon of formula (1) of claim 1 in sufficient amount to inhibit the replication of hepatitis virus present in the liver cells of a patient affected with viral hepatitis and a pharmaceutically acceptable carrier, adjuvant or excipient therefor.

9. The pharmaceutical composition of claim 8 suitable for intravenous administration.

10. A method of treating viral hepatitis in a patient suffering from viral hepatitis by administrating an amount of a conjugated interferon of formula (1) of claim 1 sufficient to inhibit the replication of hepatitis virus present in the liver cells of said patient affected with viral hepatitis.

11. The method of claim 10 wherein said conjugated interferon is administered by intravenous administration.

12. The method of claim 11 wherein the amount of a conjugated interferon of formula (1) of claim 1 sufficient to inhibit the replication of hepatitis virus present in the liver cells of said patient affected with viral hepatitis is 0.2 to 2 million international units on the basis of interferon per square meter of body surface, one time for one or two days.

13. A process for preparing a conjugated interferon of formula (1)

P-(S)x-Gal-GA-INF     (1)

wherein
P is a peptide residue of a human serum glycoprotein;
S is a sugar residue of a human serum glycoprotein
Gal is a galactose residue;
GA is a glutaraldehyde residue;
x is equal to or greater than 1; and
INF is interferon, comprising:
   providing a Cohn fraction V supernatant of human serum;
   treating the Cohn fraction V supernatant of human serum to separate alpha(1)-acid glycoprotein having the formula P-(S)x-Gal-NANA therefrom, wherein NANA is N-acetyl neuraminic acid, and recovering the alpha(1)-acid glycoprotein;
   treating the recovered alpha(1)-acid glycoprotein with neuraminidase to remove sialic acid and to obtain asialoglycoprotein of formula P-(S)x-Gal;
   linking the asialoglycoprotein with interferon by means of a glutaraldehyde (GA) crosslinking method; and recovering the conjugated interferon of formula P-(S)x-Gal-GA-INF.

14. The process of claim 13 wherein the Cohn fraction V supernatant of human serum is treated with DEAE-Sephadex or CM-Cellulose chromatography to separate the alpha(1)-acid glycoprotein of formula P-(S)x-Gal-NANA from the Cohn fraction V supernatant.

15. The process of claim 13 wherein the alpha(1)-acid glycoprotein is orosomucoid.

16. A process for preparing a conjugated interferon of formula (1)

P-(S)x-Gal-GA-INF     (1)

wherein
P is a peptide residue of a human serum glycoprotein;
S is a sugar residue of a human serum glycoprotein
Gal is a galactose residue;
GA is a glutaraldehyde residue;
x is equal to or greater than 1; and
INF is interferon, comprising;
   providing human blood serum which includes a human serum glycoprotein of the formula P-(S)x-Gal-NANA, characterized in that the residue adjacent to the sugar residue is D-galactose (Gal) and the last residue is N-acetyl neuraminic acid (NANA);
   treating the human blood serum to separate the human serum glycoprotein P-(S)x-Gal-NANA from the human blood serum and recovering the human serum glycoprotein P-(S)x-Gal-NANA;
   treating the recovered human serum glycoprotein (P-(S)x-Gal-NANA with neuraminidase to remove NANA and to obtain asialoglycoprotein (P-(S)x-Gal);
   linking the asialoglycoprotein, (P-(S)x-Gal), with interferon by means of a glutaraldehyde(GA) crosslinking method; and
   recovering the conjugated interferon of formula P-(S)x-Gal-GA-INF (1).

17. The process of claim 16 wherein the human blood serum is a Cohn fraction V supernatant of human serum and which is treated with DEAE-Sephadex or CM-Cellulose chromatography to separate the human serum glycoprotein of the formula P(S)x-Gal-NANA from the Cohn fraction V supernatant.

18. A pharmaceutical composition for treating hepatitis comprising a hepatitis-treating effective amount of a medicinal agent of claim 1 and a pharmaceutically acceptable carrier, adjuvant or excipient therefor.

19. A pharmaceutical composition of claim 18 suitable for intravenous administration.

* * * * *